(12) United States Patent
Barker et al.

(10) Patent No.: US 6,251,111 B1
(45) Date of Patent: Jun. 26, 2001

(54) JACK FOR PULLING A VERTEBRAL ANCHOR

(75) Inventors: B. Thomas Barker, Bartlett, TN (US); Thomas Zdeblick, Middletown, WI (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/421,029

(22) Filed: Oct. 20, 1999

(51) Int. Cl.[7] ................................................... A61B 17/56
(52) U.S. Cl. ..................................................... 606/61
(58) Field of Search .................................. 606/1, 60, 61, 606/86, 90, 99

(56) References Cited

U.S. PATENT DOCUMENTS

| | | | |
|---|---|---|---|
| 4,399,813 | * | 8/1983 | Barker ..................................... 606/99 |
| 4,611,581 | * | 9/1986 | Steffee ..................................... 606/61 |
| 5,312,410 | | 5/1994 | Miller et al. . |
| 5,395,374 | * | 3/1995 | Miller et al. ........................... 606/61 |
| 5,484,437 | * | 1/1996 | Michelson ............................... 606/61 |
| 5,632,765 | * | 5/1997 | Holder ................................... 606/238 |
| 5,782,831 | | 7/1998 | Sherman et al. . |

* cited by examiner

*Primary Examiner*—Gene Mancene
*Assistant Examiner*—Eduardo C. Robert
(74) *Attorney, Agent, or Firm*—Woodard, Emhardt, Naughton, Moriarty & McNett

(57) ABSTRACT

A device for pulling a vertebral anchor with a strain gauge in combination with a tension rod. The device has a cylindrical telescopic housing made of a first hollow cylinder received inside a second hollow cylinder such that the two hollow cylinders define a longitudinal passage from the proximal to the distal end of the cylindrical telescopic housing. The tension rod is slidably disposed within the longitudinal passageway and has a means mounted on or near its distal end to attach to a vertebral anchor (or bone screw). The first and second hollow cylinders are biased apart by a mechanical spring, which resides inside the second hollow cylinder. A means for moving said tension rod in a proximal direction with respect to said telescopic housing is then operatively attached to the housing, as well as, a strain gauge to directly measure the amount of tension placed on the tension rod when the device is in use.

20 Claims, 9 Drawing Sheets

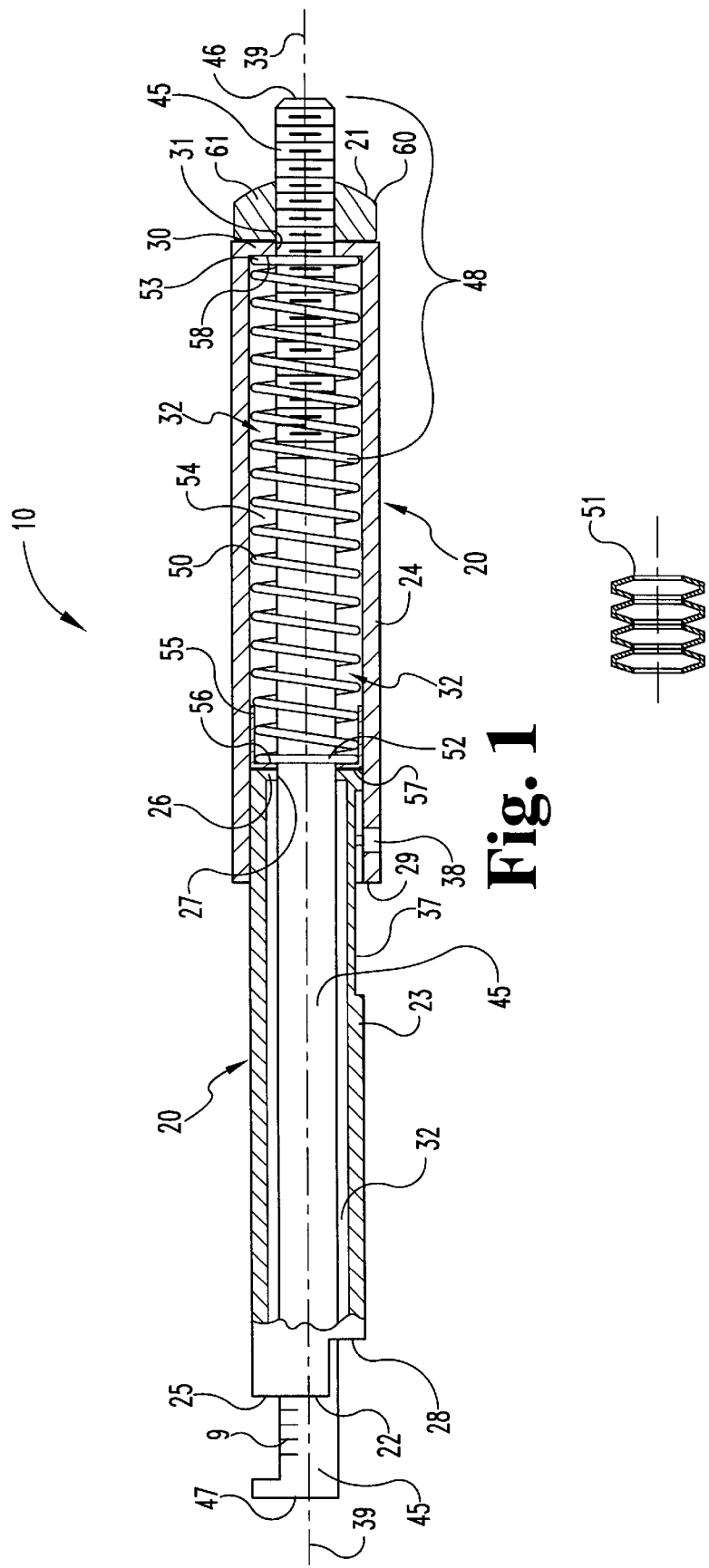

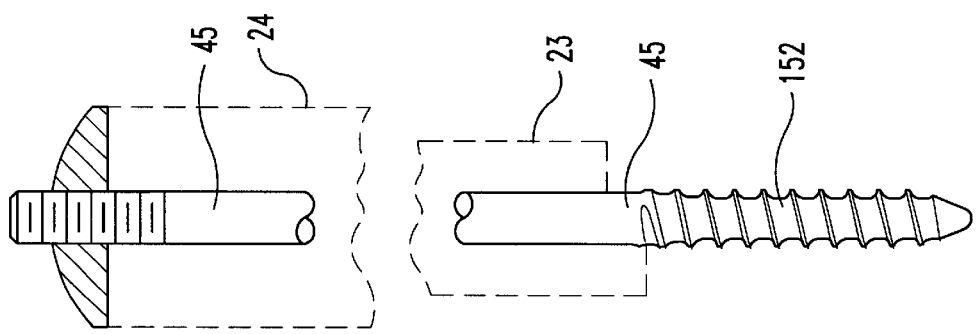
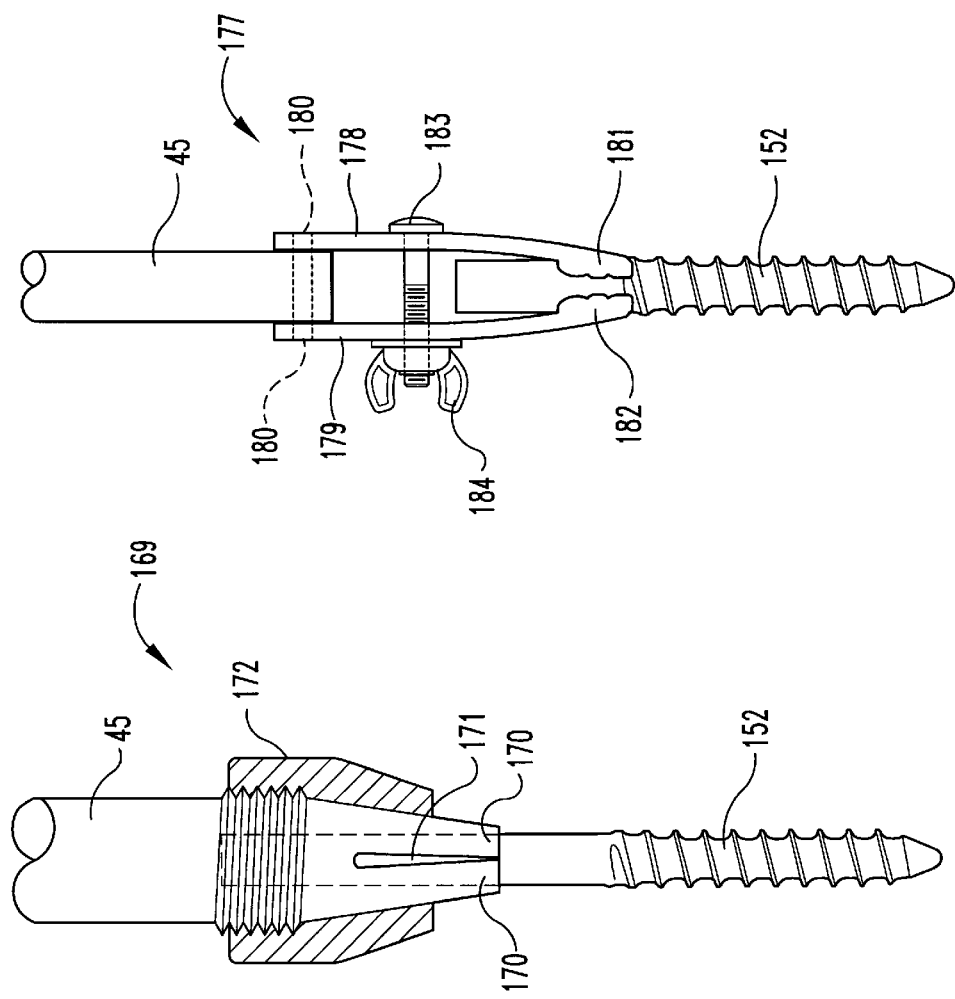
Fig. 12
Fig. 11
Fig. 10

JACK FOR PULLING A VERTEBRAL ANCHOR

This invention relates generally to orthopaedics and spinal surgery, and more particularly to an apparatus for straightening a spinal column by reducing the extent of displacement between adjacent vertebrae.

BACKGROUND OF THE INVENTION

In many cases of deformity, such as spondylolisthesis, it is desirable to reduce the extent of displacement of a vertebra prior to fusion to an adjacent vertebra. A spondylolisthesis reduction can be a technically demanding procedure requiring great care to prevent neurological impairment and damage to surrounding soft tissue. As a result, several systems have been utilized to accomplish a necessary reduction.

An early system utilized a cable system to apply force to the displaced vertebrae. One end of an extremely long cable was anchored to a vertebra and the other end was threaded through a fixture attached to the ceiling and included a series of traction weights positioned on the cable. Such a system utilizing long cables and weights external to the operating room proved unwieldy and bulky. Moreover, the surgeon could not quickly and effectively control the force applied to the vertebra.

In addition to cable systems, systems utilizing threaded shafts to draw the vertebra upwards were also used. One such apparatus for use in straightening a spinal column by reduction is presented in U.S. Pat. No. 4,611,581. The apparatus disclosed in this patent includes a pair of rigid plates positioned along the spinal column with a double threaded screw anchored in the vertebrae requiring alignment with the vertebral column. The lower portion of the screw has a cancellous thread, which engages the bone, while the upper portion has a machine thread, which passes through a slot in the plate and is capable of receiving an internally threaded nut. Upon rotation of the internally threaded nut bearing against the plate, the misaligned vertebra is drawn toward the plate as the nut advances over the machine threads on the screw. This system requires that the machine-threaded end of the screw extend through a relatively narrow slot in the plate. Such a requirement may limit the surgeon's ability to properly place the screw or may require manipulation of the vertebrae to align the screw with the slot in the plate.

Other systems have utilized a separate threaded shaft to draw the vertebrae into alignment. In such systems, the bone screw does not include a machine-threaded portion. Instead, a separate reduction mechanism grasps the head of the screw and is braced against a rod. A threaded shaft attached to the screw head pulls the misaligned vertebra toward the rod. Here again, the devices are cumbersome and difficult to maneuver into the appropriate position so the vertebra is pulled in the desired direction. Moreover, the surgeon cannot quickly and effectively control the force applied to the vertebra because he's never completely sure how much tension is being applied to the misaligned vertebra What is needed is reduction device that utilizes a rigid shaft to pull the vertebra with a device that indicates the amount of pulling force that the surgeon is exerting on the vertebra. The following is one solution to that need.

SUMMARY OF THE INVENTION

In one aspect, this invention is a device for pulling a vertebral anchor. The device has a cylindrical telescopic housing made of a first hollow cylinder received inside a second hollow cylinder such that the two hollow cylinders define a longitudinal passage from the proximal to the distal end of the cylindrical telescopic housing. A tension rod is slidably disposed within the longitudinal passageway and has a means mounted on or near its distal end to attach to a vertebral anchor (or bone screw). The first and second hollow cylinders are biased apart by a mechanical spring, which resides inside the second hollow cylinder. A means for moving said tension rod in a proximal direction with respect to said telescopic housing is then operatively attached to the housing, as well as, a strain gauge to directly measure the amount of tension placed on the tension rod when the device is in use.

In another aspect, the invention is an apparatus for use in reducing a displaced vertebra in the spine. The apparatus includes (1) a longitudinal member positionable along the longitudinal axis of a spine, (2) an anchor configured to be secured to a displaced vertebra; (3) an elongated member having a first portion attached to the anchor and a second portion; and (4) a clamping member positionable along said longitudinal member adjacent the displaced vertebra. The clamping member defines a channel for receiving the second portion of the elongated member. And the clamping member is operable between an open configuration permitting movement of the elongated member through the channel and a clamping configuration engaging the elongated member to prevent movement of the elongated member through the channel. Finally, the apparatus also includes (5) an improved device for pulling the longitudinal member or a jack, described in the preceding paragraph.

In still a further aspect, the present invention provides a method of controlled vertebral reduction. The method comprises applying a set tension, monitoring the tension over time until a substantial reduction is achieved, and increasing tension to a higher amount. The process of applying tension, monitoring for reduction and reapplying tension continues until there is no substantial reduction is tension or the desired distance of vertebral movement is achieved.

These and other objects of the invention will become apparent from the following description.

BRIEF DESCRIPTION OF THE DRAWINGS

FIG. 1 is a side view of vertebral anchor puller according to one embodiment of the present invention.

FIG. 2 is a side view of a portion of a stack of Belleville washers.

FIGS. 7–12 are side views of some alternative means for the present invention to attach to a vertebral anchor.

DESCRIPTION OF THE PREFERRED EMBODIMENTS

Figure 3:
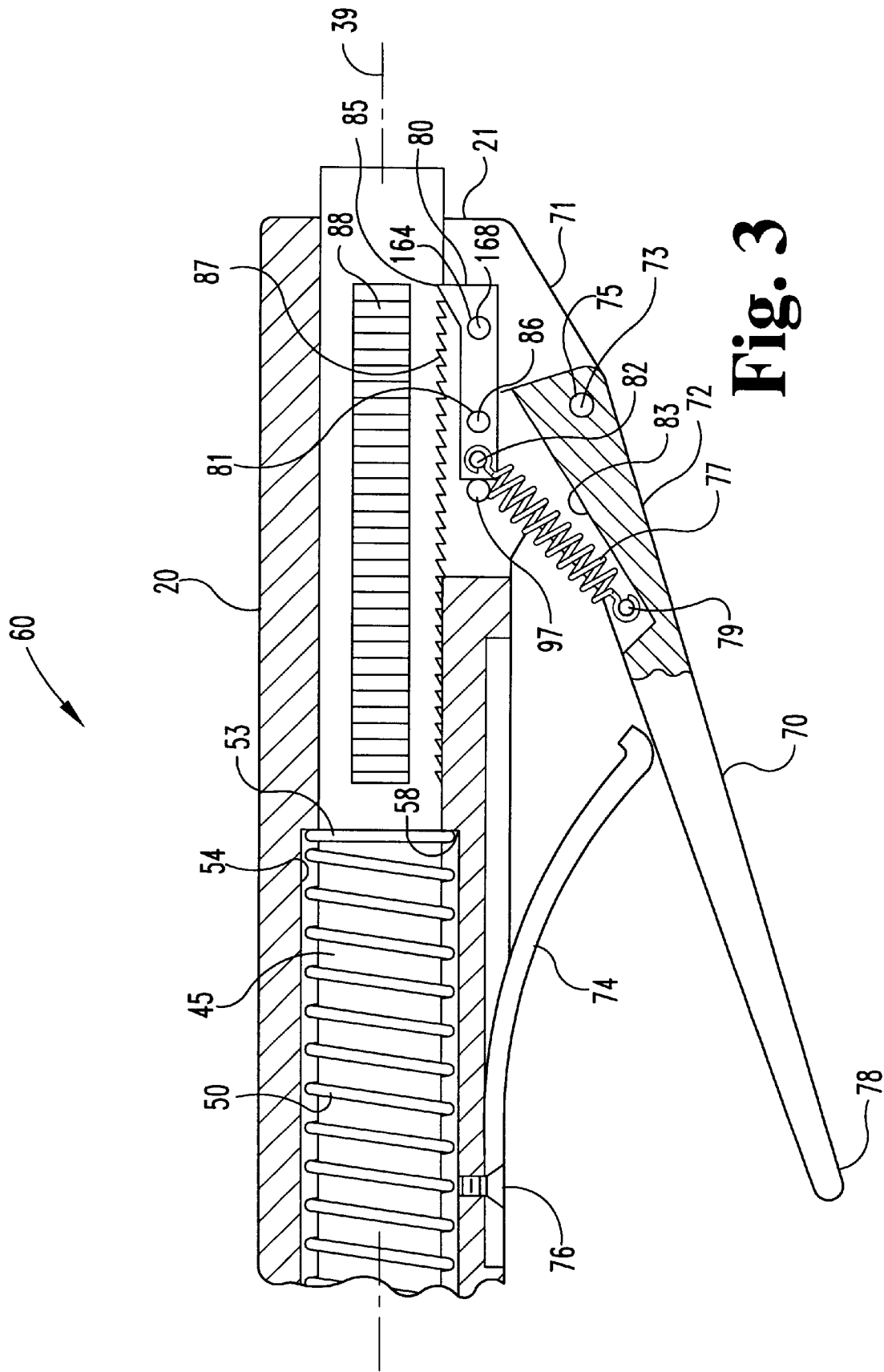
FIG. 3 is a partial side view of a ratchet means to pull the tension rod in the present invention according to an alternative embodiment of the invention.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, there is shown the inner structure of a device 10 for pulling a vertebral anchor according one preferred embodiment of the present invention. Puller 10 is built around a generally elongated cylindrical telescopic housing 20 having a proximal end 21 and a distal end 22. Telescopic housing 20 is generally formed from two hollow cylinders, 23 and 24. The proximal end 26 of hollow cylinder 23 has an annular opening 27 while the distal end 25 is preferably open with a profile 28 that preferably mates with the profile of the connector against which it is intended to be placed. Hollow cylinder 24 has an open distal end 29 and a proximal end 30 with an annular opening 31, and as shown, hollow cylinder 23 is slidably and fittingly received inside hollow cylinder 24. And together hollow cylinders 23 and 24 define a longitudinal passage 32 from proximal end 21 to distal end 22.

Puller 10 preferably has a guide groove 23 formed in the external side of hollow cylinder 23. Guide pin 38 is attached to telescopic housing 20 and extends into groove 37 thusly preventing hollow cylinder 24 from turning about centerline 39 with respect to hollow cylinder 23. Telescopic housing 20 is preferably formed in stainless steel and then machined into its final form.

A tension rod 45 is slidably received inside longitudinal passage 32. Tension rod 45 has a distal end 47, which preferably is capable of extending past distal end 22 of telescopic housing 20, and a proximal end 46, which also is preferably capable of extending past proximal end 21. Tension rod 45 includes an index scale 9 to indicate the distance distal end 47 extends beyond distal end 22. A threaded section 48 is located adjacent proximal end 21, and preferably extends along the length of rod 45 for a distance as least as long as the distance that hollow cylinder 23 telescopes into hollow cylinder 24.

A compression spring means 50 for biasing the proximal end 21 of telescopic housing 20 from its distal end 22 is preferably located inside second hollow cylinder 24, around tension rod 45. Hollow cylinder 24 defines a cylindrical cavity 54 that slidably receives a spring housing 55. Spring housing 55 is cylindrically shaped and made from stainless steel. As shown, one preferred spring or biasing means 50 is a coiled spring. The distal end 52 of the coiled spring rides against the inner wall 56, such that the end 57 of spring housing 55 is forced into abutting relationship with the proximal end 26 of hollow cylinder 23. The proximal end 53 biasing means 50 then rides against inner wall 58 of proximal end 30 of hollow cylinder 24. Besides a coiled spring other well-known or common means to bias the ends of telescopic housing 20 apart are contemplated by this invention. For example, it is also contemplated that stack of Belleville washers 51 (FIG. 2) may also be used for this purpose or a combination of a coiled spring and a stack of Belleville washers.

Still referring to FIG. 1, pulling device 10 also includes a means 60 for moving tension rod 45 in a proximal direction against the force exerted by biasing or spring means 50. As shown, one preferred means to provide this tension is a rotable tensioning wheel 61. Rotable tensioning wheel 61 has a threaded hole in its center of size to mate with threaded portion 48, which extends through annular opening 31. Situated in this manner, rotable tensioning wheel 61 is held against proximal end 24 by spring means 50 and will ride against proximal end 24 when wheel 60 is turned about centerline 39. So being, if wheel 60 is turned in one direction, rod 45 will be pulled into telescopic housing 20, and if turned in the opposite direction, rod 45 will be pushed out telescopic housing 20. The external surface of rotable tensioning wheel 45 is preferably knurled to provide a surface over which the user can have a firm grip.

Another embodiment of means 60 for moving tension rod 45 in a proximal direction, which may be mounted on device 10 is shown in FIG. 3. In this embodiment, tension rod 45 has no threaded section, but instead includes two toothed faces (racks) 87 and 88, with rack 87 on the bottom, and rack 88 on the side. Rack 87 provides the means by which tension rod 45 is moved in a proximal direction with respect to housing 20. Tension rod 45 is moved by utilizing lever actuator 70, which is pivotally mounted between housing sidewalls 71. In particular, base 72 of lever actuator 70 includes a pivot bore 75 that receives lever pin 73. Base 72 of lever actuator 70 substantially fills the space between housing sidewalls 71. The ends of lever pin 73 are mounted in sidewalls 71 such that lever actuator 70 is capable of pivoting about lever pin 73. A lever return spring 74 is attached to telescopic housing 20 via screw 76 and serves to bias the tensioning handle portion 78 of lever actuator 70 to its extended position as shown in FIG. 3. Lever actuator 70 is then pivoted about lever pin 73 simply by depressing handle portion 78 toward housing 20.

Base 72 of lever actuator 70 includes a groove 83 that is intercepted by a pair of axially aligned pivot bores (not shown) in the base, one on either side of grooves 83. A pawl 80 is partially received within groove 83 and includes a pivot bore 81 that aligns with above-mentioned pivot bores in the base 72 of lever actuator 70. Pawl 80 is pivotally mounted to lever actuator 70 via a pawl attachment pin 86 whose ends are received within the pivot bores made on either side of groove 83 and pivot bore 81 of pawl 80. Thus, pawl 80 is pivotally mounted to lever actuator 70 by pin 86. A tensioning spring 77 is mounted between spring anchor pin 82 of pawl 80 and spring anchor pin 79 of lever actuator 70. Tension spring 77 biases tooth engagement surface 85 of pawl 80 into contact with rack 87 of tension rod 45. A backstop pin 97 is mounted between sidewalls 71 of housing 20 and serves as a backstop for pawl 80. Each depression of tensioning handle 78 causes pawl 80 to move parallel to centerline 39 in a direction toward proximal end 21. The action of lever actuator 70 and pawl 80 causes rack 80 to be moved with respect to housing 20. Both lever actuator 70 and pawl 80 are preferably machined from stainless steel, as well as, tension rod 45.

Figure 4:
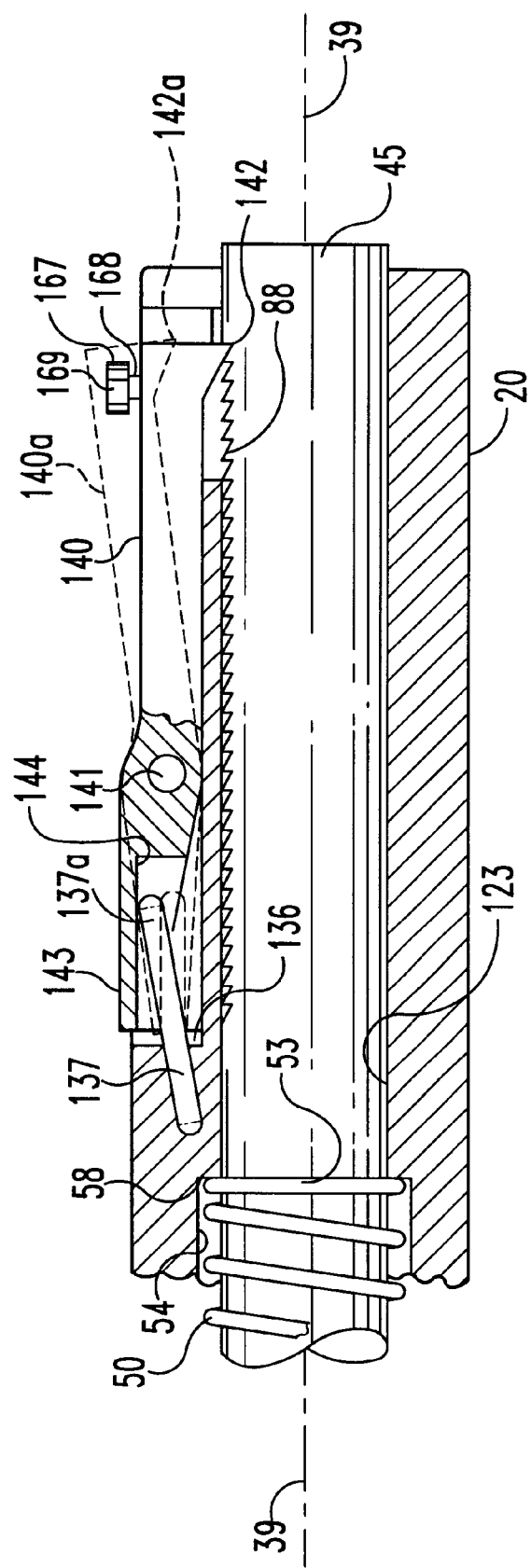
FIG. 4 is a partial top view of ratchet brake according to an alternative embodiment of the invention.
Figure 5:
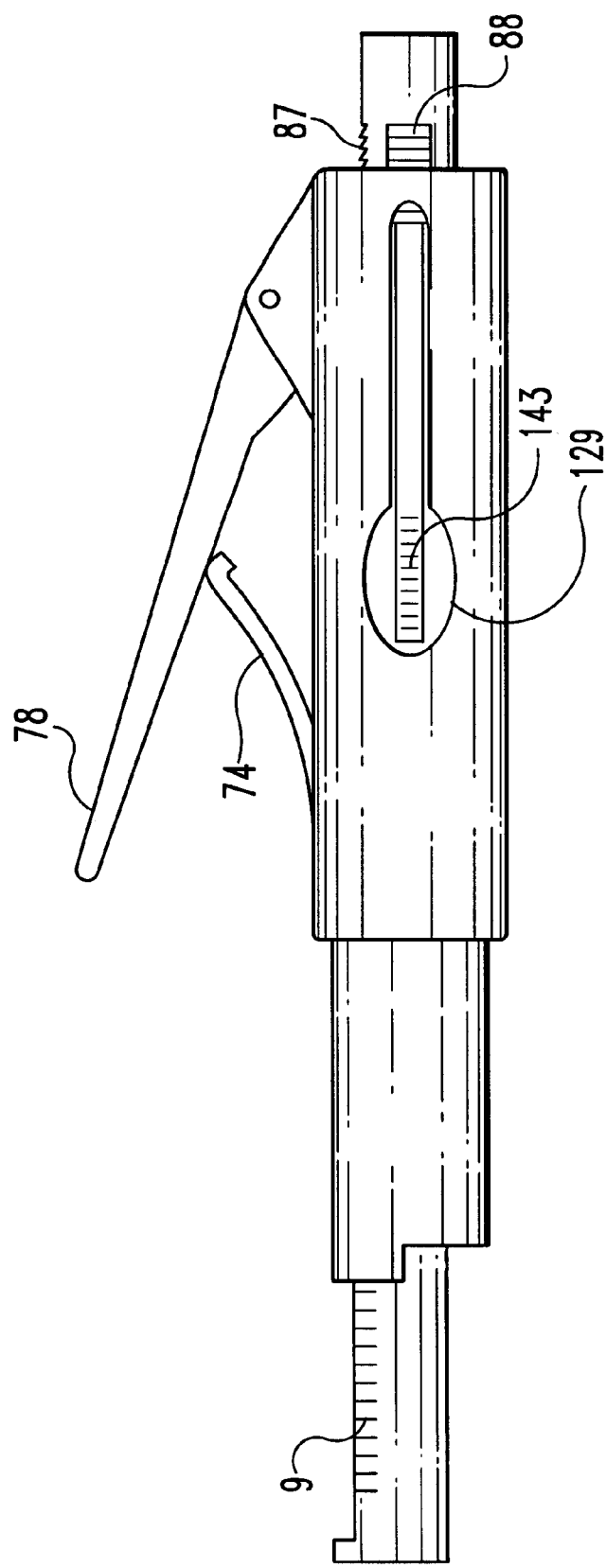
FIG. 5 is top view of a vertebral anchor puller according to one embodiment of the present invention.

Referring now to FIG. 4, a rack lock 140 is provided and serves as a means for locking tension rod 45 against movement into telescopic housing 20. For this purpose, and in addition to the first rack 87, tension rod 45 also includes the second rack 88 arranged orthogonally with respect to first rack 87. In other words, it is often on the side of tension rod 45. An elongated groove 136 is cut into the side of telescopic housing 20 adjacent rack 88. An elongated rack lock 140 is pivotally mounted in groove 136 via pivot pin 141, which spans groove 136 and whose ends are mounted in the walls of groove 136. Thus, rack lock 140 can pivot between a locked position in which tooth engagement surface 142 engages the teeth of rack 88, and a release position illustrated in broken lines 140a in FIG. 4. The proximal end of groove 136 opens into bore 123 of housing 20 such that tooth engagement surface of rack lock 140 can engage the teeth of rack 88. A cavity at the rear end of rack lock 140 provides a spring guide surface 144 that receives a portion of lock spring 137, which is preferably a short segment of spring wire or rod. Spring 137 is snug fit in a socket in the end wall of groove 136 as shown in FIG. 4. Because the other end of spring 137 rests against the surface of spring guide 144, rack lock 140 is naturally urged to its locked position. However, rack lock 140 can be moved to its release position by depressing release surface 143 into oval cutout 129 (FIG. 5) of housing 20 toward axis 32 such that return spring 137, rack lock 140 and tooth engagement surface 142 are moved to their release positions designated respectfully as 137a, 140a and 142a.

In this second embodiment of moving means 60, pawl 80 normally prevents tension rod 45 from telescoping distally out of housing 20. This is accomplished because tension spring 77 normally urges tooth engagement surface 85 of pawl 80 into engagement with the teeth of rack 87. In order to move tension rod 45 out from housing 20, both rack lock 140 and pawl 80 must be disengaged from their respective cooperating toothed surfaces or racks 88 and 87. As presented above, rack lock 140 is moved to its release position simply by depressing release surface 143. With regard to pawl 80, a pawl release pin 167 includes a head portion 169 and a shaft 168 which extends through a slot (not shown) in one of the housing side walls 71 and is press fitted in a hole 164 of pawl 80. When head 169 of pawl release pin 167 is pushed away from centerline 39, the tooth engagement surface 85 of pawl 80 is pushed away from rack 87.

Figure 6:
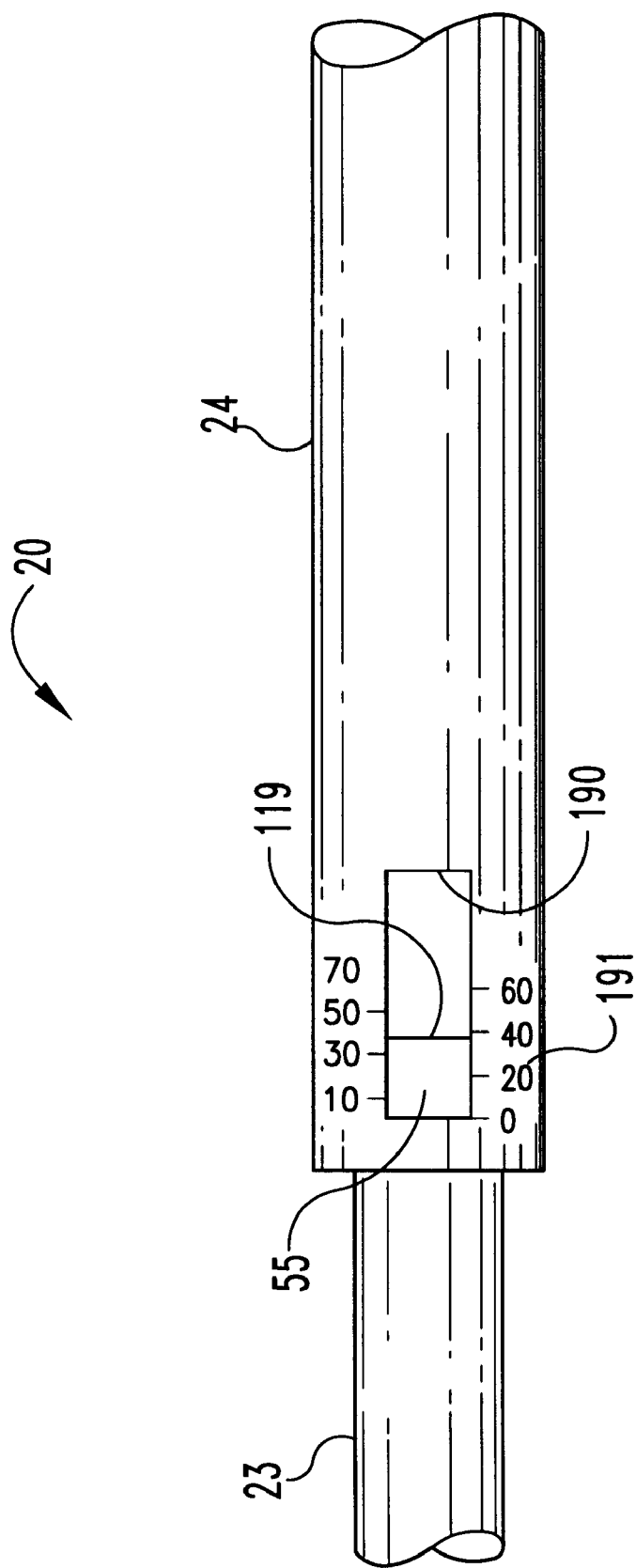
FIG. 6 is a side view of the strain gauge element of the present invention.

In a most preferred embodiment, device 10 also includes a means to gauge the tension applied to tension rod 45 when device 10 is attached to and pulling on a vertebral anchor. As previously presented, hollow cylinder 23 has a proximal end 26 that is slidably and telescopically received in at least a portion of hollow cylinder 24. Spring housing 55 abuts against proximal end 26, and due to force of compression spring biasing means 50, spring housing 55 and hollow cylinder 24 move within cylindrical cavity 54 as a single unit whenever rod 45 and a vertebral anchor is pulled in a proximal direction. So being, in one preferred embodiment the scale means is formed by placing at least one window 190 in cylinder 24 that opens onto the exterior surface of spring housing 55. (FIG. 6.) Scale markings 191 in user defined graduations are then located adjacent window 190, and spring housing 55 includes a reference mark 119 that moves when hollow cylinder 23 telescopically moves into hollow cylinder 24. Accordingly and upon calibration of markings 191, reference mark 119 will move in window 190 in proportion to the tension that is placed upon tension rod 45 and inform the user of device the amount of force pulling means 60 is placing on a vertebral anchor. Additionally, scale markings 9 provide an indication of the distance the tension rod has moved with respect to the housing. Further details of a ratcheting assembly and a scale means can be found in U.S. Pat. No. 5,312,410 to Miller et al. the disclosure of which is specifically incorporated by reference.

Tension rod 45 further includes a means for attaching device 10 to a vertebral anchor (or bone-engaging fastener). In this regard, the vertebral anchor is a bone screw, particularly a Schantz-type bone screw. And the means for attaching to the vertebral anchor (or bone engaging fastener) is one of many known mechanical couplings that are known to connect two rods that are placed in tension. Several examples follow.

Figure 7:
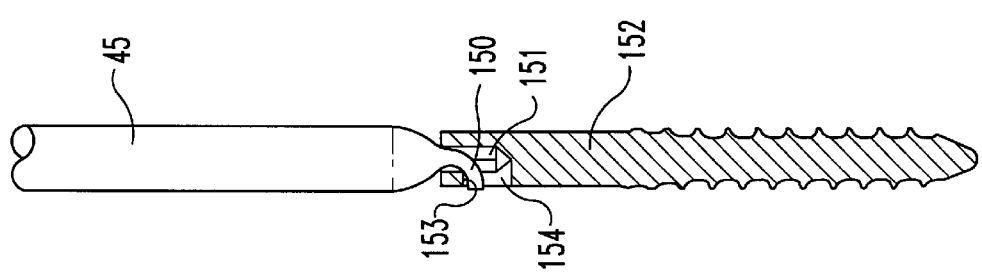

In one embodiment the attachment means is a hook, of which one particularly preferable embodiment is shown in FIG. 7. In this particular embodiment, the distal end of tension rod 45 tapers to a hook 150. The proximal end of vertebral anchor 152 has a female cavity 151 with a groove 154 cut into the sidewall of female cavity 151. Hook 150 is then placed inside female cavity 151 and into groove 154. Interlocked in this manner, the user may then apply an upward force on vertebral anchor 152 by pulling on rod 45. An upward pulling force applied to rod 45 is transferred to ledge 153 inside groove 45, which in turn, applies the upward pulling force to vertebral anchor 152.

Figure 8:
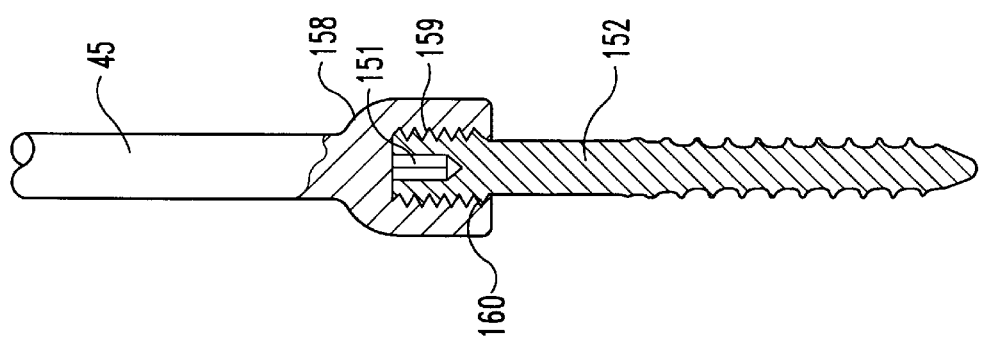

In another embodiment the attachment means are mutually engaging screw threads, of which one particularly preferable embodiment is shown in FIG. 8. In this particular embodiment, the distal end of tension rod 45 ends with a drum 158, and the distal end of drum 158 contains a threaded chamber 159. Threaded chamber 159 is then threaded down over a corresponding set of male threads 160, which are located on the proximal end of vertebral anchor 152. Attached in this manner, an upward pulling force applied to rod 45 is transferred through mutually engaging screw threads 159 and 160, which in turn, applies the upward pulling force to anchor 152.

Figure 9:
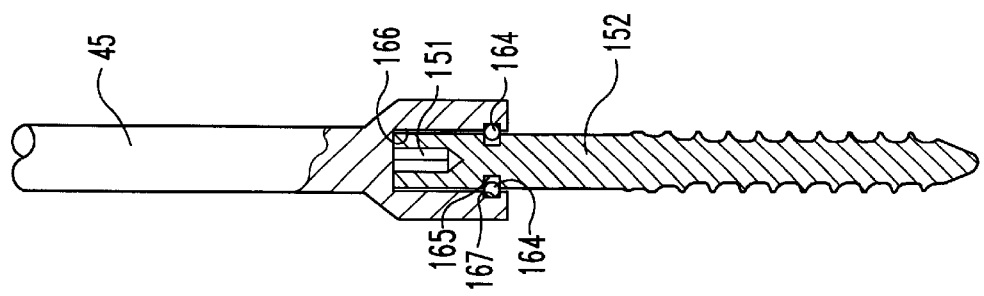

In a third embodiment, the attachment means is a snap ring, of which one particularly preferable embodiment is shown in FIG. 9. In this particular embodiment, vertebral anchor 152 has an annular groove 165, preferably close to its proximal end. The distal end of rod 45 has a bore 166 that slidingly engages the proximal end of vertebral anchor 152. Bore 166 also has an annular groove 167 that may reside at the same elevation as annular groove 165 of vertebral anchor 152 when the distal end of rod 45 is placed over the vertebral anchor. A snap ring 164 is then used to hold vertebral anchor 152 to rod 45. Preferably, snap ring 164 is slightly compressed and slid through a window (not shown) in the side of groove 167. Once in place, snap ring 167 is then slightly expanded through the wings of the snap ring (not shown) that extend from this window and snap ring 167 and bore 166 are slid over the proximal end of vertebral anchor 152. Thereafter, snap ring 164 is simply allowed to relax when annular grooves 165 and 167 reach the same elevation. Attached in this manner, an upward pulling force applied to rod 45 is transferred through snap ring 164 on to anchor 152.

A fourth embodiment of the attachment means is a collet, of which one particularly preferable embodiment is shown in FIG. 10. In this particular embodiment, the collet 169 is an integral part of rod 45. Collet 169 includes a plurality of resilient collet segments 170 for gripping the proximal end of vertebral anchor 152, which are separated by a plurality of axially extending slots 171. A lock nut 172 is then used to defect the collet segments radially inward to grip the proximal end of vertebral anchor 152. Attached in this manner, an upward pulling force applied to rod 45 is transferred through the collet segments 170 on to anchor 152.

Yet a fifth embodiment of the attachment means is a pincher, of which one particularly preferable embodiment is shown in FIG. 11. In this particular embodiment, pincher 177 is attached to the distal end of rod 45. Pincher 177 has two handles 178 and 179 that are held to rod 45 by pin 180. The distal end of handles 177 and 178 have two grasping claws, respectively 181 and 182. Grasping claws 181 and 182 are held around vertebral anchor 152 by a threaded screw 183 that passes through both handle 178 and handle 179 and wing nut 184. Pincher 177 is then tightened around vertebral anchor 152 by tightening wing nut 184 on threaded screw 183. Attached in this manner, an upward pulling force applied to rod 45 is transferred through the claws 181 and 182 on to anchor 152.

Still another attachment means is a tension rod 45 with an integral vertebral anchor 152 formed on its distal end, of which one particularly preferable embodiment is shown in FIG. 12. In this particular embodiment, tension rod 45 and vertebral anchor are cast and/or machined from a common piece of material. As a result, no mechanical fittings are required because an upward pulling force applied to rod 45 is directly transferred to the anchor portion 152, which is a part of rod 45.

Figure 13:
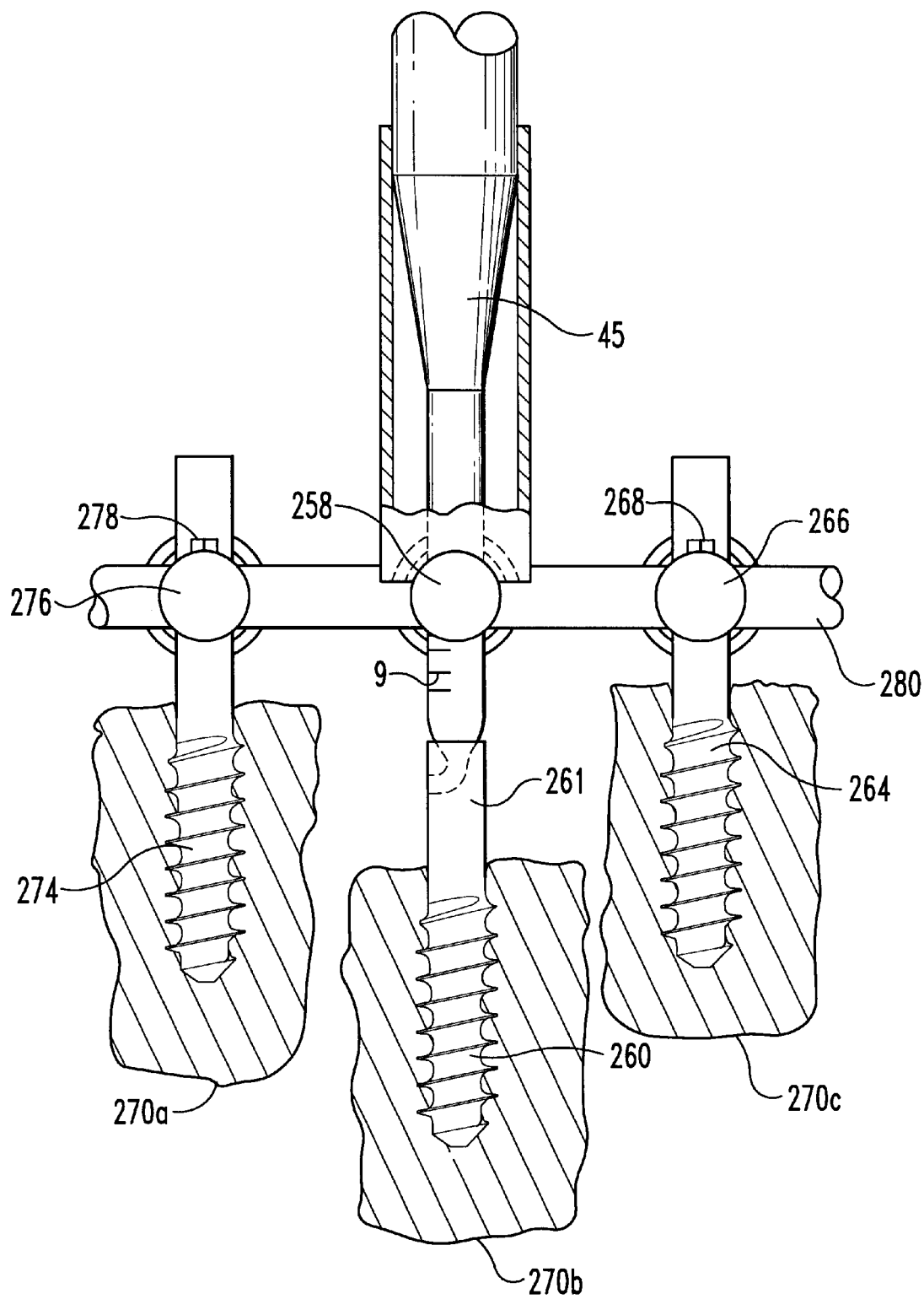
FIG. 13 is an illustration of the application of the vertebral anchor puller according to one embodiment of the present invention.
Figure 14:
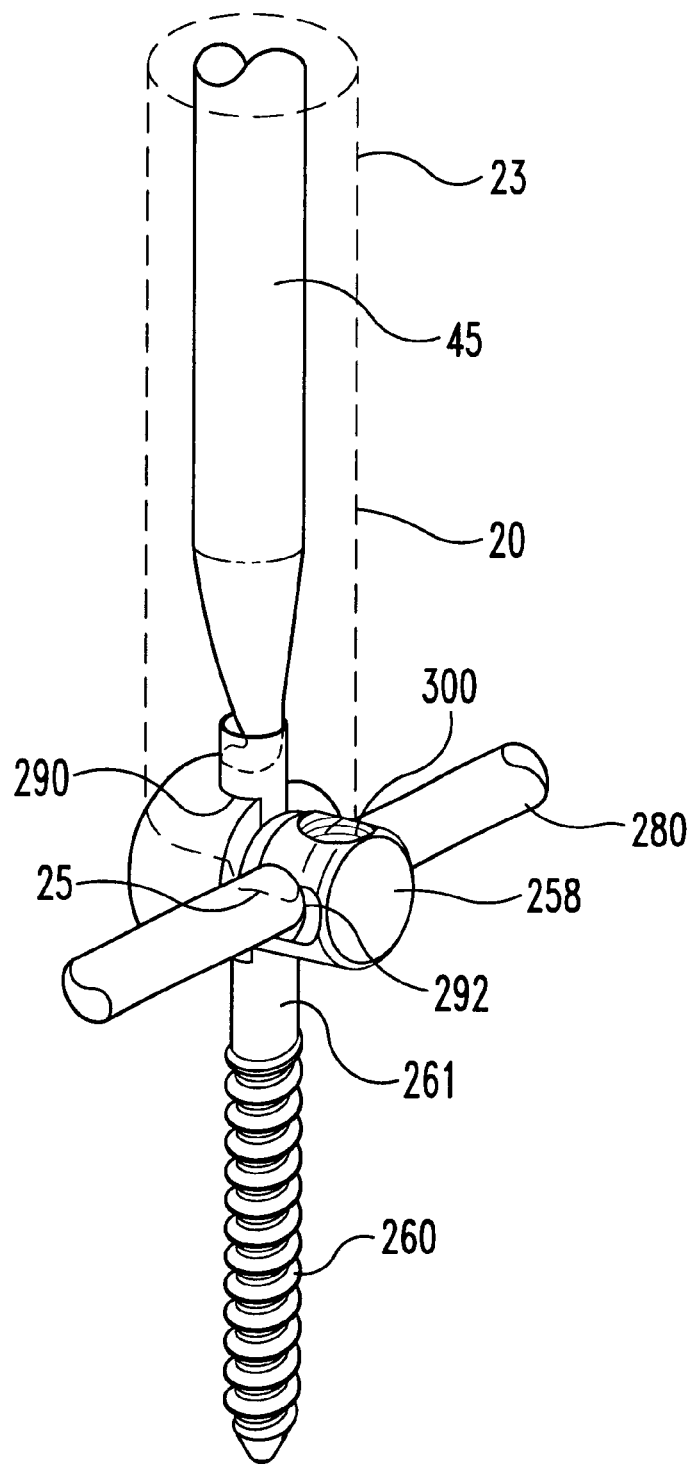
FIG. 14 is a side view of the embodiment shown in FIG. 13.

Referring now to FIGS. 13 and 14, a reduction apparatus according to yet another embodiment of the invention is shown. A longitudinal member such as spinal rod 280 spans vertebra 270a, 270b and 270c. The rod can be anchored at either end to vertebrae 270a and 270c by a connector assembly consisting of bone bolts ("vertebral anchors") 264 and 274 anchored into respective vertebrae. Rod connector members 266 and 276 are attached to rod 280 and are attached to bone bolts 264 and 274 by set screws 268 and 278 respectively. Additional details of this type connector can be found in U.S. Pat. No. 5,947,967 to Barker, the disclosure of which is expressly incorporated by reference. By way of example, the connector assemblies anchoring the rod can include Schantz-type bolts and rod-bolt connectors, which are commercially available from Medtronic Sofamor Danek. Moreover, although this embodiment utilizes bone bolts and rod connectors to anchor the ends of rod 80, it is contemplated that other means such as hooks, could be used to anchor the rod to the adjacent vertebra to provide a platform for drawing the misaligned vertebra 270b toward rod 280. Still further, it is contemplated that rod 280 could be substituted by a plate or a rod-plate combination.

Referring more specifically to the reduction apparatus, an anchoring element such as a Schantz-type bone screw 260 is preferably anchored into intermediate vertebra 270b. Attached to rod 280 is a rod connector 258 having a channel 290 (FIG. 14) disposed therein for receiving shank portion 261 of bone bolt 260. As illustrated in FIG. 13, tension rod 45 is extended from device 10 and attached to bone screw 260 with the distal end 22 of telescopic housing 20 riding on the top surface of rod connector 258. Situated in this fashion, tool 10 can be used to pull vertebra 270b into alignment with the adjacent vertebrae 270a and 270b. As tensioning force is transmitted to rod 45 (rotating tension wheel 61 or operating lever actuator 70), device 10 engages rod connector 258, which ultimately bears against rod 280 anchored the adjacent vertebrae. In this manner, the device 10 uses rod 280 for leverage to pull displaced vertebra toward the rod. In this regard it is further contemplated that for some applications device 10 could be adapted to directly engage rod 280.

Referring now to FIG. 14, the reduction apparatus of FIG. 13, is shown from the side with bone bolt 260 drawn into slot 290 of the rod connector 258. Additionally, these figures show that rod connector 258 has a passage 292 to accept rod 280 that can be maintained in place on the rod by a set screw (not shown) placed in threaded hole 300. It is contemplated that any type of rod connector can be acceptable to support device 10, and that the disclosure of the above rod connector is not intended to be limiting in any manner. Additional details of operating a reduction device are disclosed in the U.S. Pat. No. 5,782,831 the disclosure of which is expressly incorporated into this specification by reference.

In use, the tensioning device may be used to pull a vertebra towards rod 280. In a preferred aspect, tool 10 may be used to pull the vertebra toward the rod from a plurality of angles, in multiple planes. Additionally, for the embodiment of FIG. 1, tool 10 may also be used to push the anchor in a given direction. This may be useful with two rods positioned bi-laterally. A first tool may pull a first anchor while a second tool pushes a second anchor, thereby realigning the vertebra. Still more preferably, tool 10 may be utilized to perform vertebral reduction over an extended period of time with minimal reducing force. This may have the advantage of more slowly stretching ligaments, muscles and other connecting tissue, as well as the prevention of trauma to the spinal cord as a result of abrupt reduction of the vertebra. In previous methods, reduction of the vertebra is conducted in a single movement with the maximum amount of force necessary to force the vertebra into a new position. Patient reaction, particularly neural damage, may be monitored during procedure with the reduction stopped if monitors indicate neurological damage to the patient. The present invention provides a method of vertebral reduction relying on varying distance, force, and time to achieve a safe vertebral reduction. As an example, vertebra reduction may be accomplished over a period of time without exceeding a very low amount of force. Typically, the force which may be required for reduction with the apparatus of the present invention can be seventy-five percent or less than that required for immediate reduction in a single movement.

Initially a low level of force for interval reduction is determined. Tool 10 is engaged with anchor 261 and the predetermined amount of force is applied. The initial distance of movement in response to the force is recorded based on scale 9. The time is also recorded. The tension applied by tool 10 is monitored over time until the tension is substantially reduced, preferably approaching zero. The process of tensioning to a predetermined tension, recording distance and time (if desired), and waiting for reduction in tension over time, is continued until either tension no longer substantially reduces over time or the appropriate distance of reduction is achieved.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A device for pulling a vertebral anchor, comprising:

(a) a cylindrical telescopic housing, said telescopic housing having a longitudinal passageway therethrough, a proximal end, and a distal end; said telescopic housing including a first hollow cylinder and a second hollow cylinder wherein said second hollow cylinder is telescopically received inside said first hollow cylinder;

(b) a tension rod slidably disposed within said longitudinal passageway;

(c) means, mounted on said tension rod for attaching to a vertebral anchor;

(d) means for biasing the proximal end of said telescopic housing away from the distal end of said telescopic housing;

(e) scale means, mounted on said telescopic housing, for directly measuring and indicating the amount of tension in said tension rod; and (f) means for moving said tension rod in a proximal direction with respect to said telescopic housing.

2. The device of claim 1 wherein said tension rod has a threaded section and said means for moving said tension rod includes a rotable tensioning wheel, movably connected to said telescopic housing, having a threaded aperture threadably engaging said threaded section, whereby rotation of said tensioning wheel forces said tensioning rod to move with respect to said telescopic housing.

3. The device of claim 1 wherein said tension rod includes a rack with a plurality of teeth on one side and said means for moving said tension rod includes a pawl engageable with said teeth of said rack and a lever actuator pivotally mounted to said telescopic housing and attached to said pawl, whereby pivoting said lever actuator ratchets said tensioning rod to move with respect to said telescopic housing.

4. The device of claim 3, including means, attached to said telescopic housing, for locking said tension rod against movement in a distal direction with respect to said telescopic housing.

5. The device of claim 1 wherein said scale means includes a spring housing movably mounted within said telescopic housing and scale markings on said telescopic housing, said spring housing being biased to a zero position by said biasing means but being capable of moving away from said zero position a distance proportional to the tension in said tension rod, said scale indicating the distance that said scale member is away from said zero position.

6. The device of claim 1 wherein said biasing means is a stack of Belleville washers positioned between said first and second hollow cylinders.

7. The device of claim 1, wherein said biasing means is a spring positioned between said first and second hollow cylinders.

8. The device of claim 1 wherein said means for attaching to a vertebral anchor includes a hook.

9. The device of claim 1 wherein said means for attaching to a vertebral anchor includes screw threads.

10. The device of claim 1 wherein said means for attaching to a vertebral anchor includes a collar and a snap ring.

11. The device of claim 1 wherein said means for attaching to a vertebral anchor includes a collet.

12. The device of claim 1 wherein said means for attaching to a vertebral anchor includes pinchers.

13. The device of claim 1 including a vertebral anchor and wherein said means for attaching to a vertebral anchor includes a contiguous connection wherein said tension rod and said anchor or made of a common piece of material.

14. An apparatus for use in reducing a displaced vertebra in the spine, including a longitudinal member positionable along the longitudinal axis of a spine; an anchor configured to be secured to a displaced vertebra; an elongated member having a first portion attached to said anchor and a second portion; a clamping member positionable along said longitudinal member adjacent the displaced vertebra, said clamping member defining a channel for receiving said second portion of said elongated member, said clamping member operable between an open configuration permitting movement of said elongated member through said channel and a clamping configuration engaging said elongated member to prevent movement of said elongated member through said channel, and a jack, wherein the improvement comprises a jack having:

(a) a cylindrical telescopic housing, said telescopic housing having a longitudinal passageway therethrough, a proximal end, and a distal end; said telescopic housing including a first hollow cylinder and a second hollow cylinder wherein said second hollow cylinder is telescopically received inside said first hollow cylinder;

(b) a tension rod slidably disposed within said longitudinal passageway;

(c) means, mounted on said tension rod, for attaching to a vertebral anchor;

(d) means for biasing the proximal end of said telescopic housing away from the distal end of said telescopic housing;

(e) scale means, mounted on said telescopic housing, for directly measuring and indicating the amount of tension in said tension rod; and (f) means for moving said tension rod in a proximal direction with respect to said telescopic housing.

15. The device of claim 14 wherein said tension rod has a threaded section and said means for moving said tension rod includes a rotable tensioning wheel, movably connected to said telescopic housing, having a threaded aperture threadably engaging said threaded section, whereby rotation of said tensioning wheel forces said tensioning rod to move with respect to said telescopic housing.

16. The device of claim 14 wherein said tension rod includes a rack with a plurality of teeth on one side and said means for moving said tension rod includes a pawl engageable with said teeth of said rack and a lever actuator pivotally mounted to said telescopic housing and attached to said pawl, whereby pivoting said lever actuator ratchets said tensioning rod to move with respect to said telescopic housing.

17. The device of claim 16, including means, attached to said telescopic housing, for locking said tension rod against movement in a distal direction with respect to said telescopic housing.

18. The device of claim 14 wherein said biasing means is a stack of Belleville washers positioned between said first and second hollow cylinders.

19. The device of claim 14, wherein said biasing means is a spring positioned between said first and second hollow cylinders.

20. The device of claim 14 wherein said means for attaching to a vertebral anchor includes a hook.

\* \* \* \* \*